United States Patent
Popov et al.

(10) Patent No.: US 9,835,537 B2
(45) Date of Patent: Dec. 5, 2017

(54) METHOD FOR DETERMINING PORE SPACE PARAMETERS AND A THERMAL CONDUCTIVITY OF A MATRIX OF POROUS MATERIALS

(71) Applicant: Schlumberger Technology Corporation, Sugar Land, TX (US)

(72) Inventors: Yury Anatolievich Popov, Moscow (RU); Irina Bayuk, Moscow (RU); Anton Vladimirovich Parshin, Bashkortostan (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 394 days.

(21) Appl. No.: 14/394,238

(22) PCT Filed: Apr. 12, 2013

(86) PCT No.: PCT/RU2013/000315
§ 371 (c)(1),
(2) Date: Oct. 13, 2014

(87) PCT Pub. No.: WO2013/154469
PCT Pub. Date: Oct. 17, 2013

(65) Prior Publication Data
US 2015/0049784 A1    Feb. 19, 2015

(30) Foreign Application Priority Data

Apr. 13, 2012   (RU) .................. 2012114703

(51) Int. Cl.
*G01N 25/18* (2006.01)
*G01N 15/08* (2006.01)

(52) U.S. Cl.
CPC ......... *G01N 15/088* (2013.01); *G01N 15/082* (2013.01); *G01N 25/18* (2013.01); *G01N 2015/0833* (2013.01)

(58) Field of Classification Search
USPC .......................................... 374/45, 136, 44
See application file for complete search history.

(56) References Cited

U.S. PATENT DOCUMENTS

| 5,159,569 A | 10/1992 | Xu et al. |
| 2008/0202220 A1 | 8/2008 | Schmidt |

(Continued)

FOREIGN PATENT DOCUMENTS

RU    2334977 C2    9/2008

OTHER PUBLICATIONS

Bayuk, et al., "Identification of the Fluid Type in a Reservoir Rock", Journal of the Solid Earth, vol. 35, No. 11, 1999, pp. 917-923.

(Continued)

*Primary Examiner* — Mirellys Jagan

(57) ABSTRACT

A porous sample is alternately saturated with at least two saturating fluids with known different thermal conductivities. As at least one saturating fluid a mixture of at least two fluids is used with known and different thermal conductivities. After each saturation thermal conductivity of the saturated sample is measured, and pore space characteristics and matrix thermal conductivity are determined based on the results of thermal conductivity measurements.

15 Claims, 1 Drawing Sheet

(56) References Cited

U.S. PATENT DOCUMENTS

| | | | |
|---|---|---|---|
| 2014/0056326 A1* | 2/2014 | Skibin | G01N 25/18 374/44 |
| 2015/0010037 A1* | 1/2015 | Vafai | G01K 17/20 374/29 |
| 2015/0168323 A1* | 6/2015 | Popov | G01N 25/18 374/44 |

OTHER PUBLICATIONS

Bayuk, et al., "Upper and lower stiffness bounds for porous anisotropic rocks", Geophysical Journal International, vol. 175, Issue 3, Dec. 2008, pp. 1309-1320.

Popov, et al., "Interrelations Between Thermal Conductivity and Other Physical Properties of Rocks: Experimental Data", Pure and Applied Geophysics, vol. 160, Issue 5-6, May 2003, pp. 1137-1161.

Popov, et al., "Physical properties of rocks from the upper part of the Yaxcopoil-1 drill hole, Chicxulub crater", Meteoritics & Planetary Science, vol. 39, Issue 6, Jun. 2004, pp. 799-812.

\* cited by examiner

METHOD FOR DETERMINING PORE SPACE PARAMETERS AND A THERMAL CONDUCTIVITY OF A MATRIX OF POROUS MATERIALS

FIELD OF THE INVENTION

The disclosure relates to studying physical properties of heterogeneous porous materials, namely, to determining pore space parameters and thermal conductivity of matrix (a space filled by solid substance only) of such materials.

The heterogeneous porous materials may include, for instance, industrial materials, loose and consolidated rock samples, and minerals.

BACKGROUND ART

A known method for determining pore space properties and matrix thermal conductivity in a porous material sample consists in measuring thermal conductivity of the sample alternately saturated by three fluids with different thermal conductivity (Popov et al. Interrelations between Thermal Conductivity and Other Physical Properties of Rocks: Experimental Data, Pure and Applied Geophysics., 160, 2003, pp. 1137-1161). The method is based on determination of porosity of the porous material sample and shapes of pores and cracks simulated by spheroids and characterized by a single aspect ratio. Porosity of the porous sample, thermal conductivity of its matrix, and the aspect ratio of pore and crack simulating spheroids are determined through solving three non-linear equations with three unknowns, using thermal conductivity values as measured in the porous sample alternately saturated by the three fluids with known different thermal conductivity. Equations in that system are equalities of theoretical and experimental thermal conductivity values of porous samples successively saturated by three fluids with known and different thermal conductivity. Theoretical values of thermal conductivity are determined by a known method based on a self-consistent effective-medium theory which allows for thermal conductivity of a porous material to be expressed as a function of thermal conductivity of its matrix, the fluid saturating its pores and cracks, porosity and the aspect ratio of spheroids. The disadvantages of the method are as follows: (1) a single aspect ratio is used to characterize pore shapes and cracks, even though their actual aspect ratios differ by several orders of magnitude, (2) the method requires successive saturation of a porous material sample with three fluids with thermal conductivity meeting the three following criteria: a) it should be known for each fluid used; b) it should have materially different values, each of which should be pre-selected in conformity with certain requirements regarding thermal conductivity, porosity and pore space parameters of heterogeneous porous materials under study; c) thermal conductivity values of the three fluids in question should be within a certain range pre-selected depending on thermal conductivity, porosity and pore space parameters of heterogeneous porous materials under study. Meeting the last three criteria is a serious challenge because of a shortage of such fluids in the natural environment. Furthermore, that well-known method has the disadvantage of insufficient accuracy of definition of pore space parameters and matrix thermal conductivity because it is limited to measurements of merely thermal conductivity of fluid-saturated heterogeneous porous material, and fails to use measured values of other physical properties, which may include, for instance, velocities of longitudinal and shear elastic waves, electric conductivity, hydraulic and dielectric permeability, density, and volumetric thermal capacity.

There is also known a method for characterizing pore space and thermal conductivity of a matrix (Popov et al. Physical Properties of Rocks from the Upper Part of the Yaxcopoil-1 Drill Hole, Chicxulub Crater, Meteoritics & Planetary Science, 39, #6, 2004, pp. 799-812) which comprises successive saturation of a porous sample with at least two fluids with known different thermal conductivities to determine porosity of the sample. Each time after the porous sample is saturated by a fluid its thermal conductivity is measured, and a combination of measured thermal conductivity and porosity values of the porous sample of a known ratio are used to determine pore space and thermal conductivity of the porous sample matrix.

That known method has the following disadvantages: (1) more than two unknowns are determined from merely two thermal conductivity measurements, which may result in a fairly wide range of solutions in determining pore space parameters and matrix thermal conductivity; (2) porosity should be preliminary known; (3) the method requires successive saturation of a porous material sample with two different fluids with thermal conductivity meeting the following criteria: a) it should be known for each fluid; b) it should be materially different within a pre-selected range in conformity with thermal conductivity, porosity, and pore space parameters of heterogeneous porous materials under study. Meeting the last two criteria is a serious challenge because of a shortage of such fluids in the natural environment. Furthermore, a disadvantage of that well-known technique is insufficient accuracy of definition of pore space parameters and matrix thermal conductivity because it is limited to measurements of merely thermal conductivity of fluid-saturated heterogeneous porous material, and fails to use measured values of other physical properties, which may include, for instance, velocities of longitudinal and shear elastic waves, electric conductivity, hydraulic and dielectric permeability, density, and volumetric thermal capacity.

SUMMARY

The disclosure provides for improved sustainability of definition of pore space characteristics and thermal conductivity of a matrix through the use of mixtures of two or more fluids with different thermal conductivities as additional saturating fluids. In that way, heterogeneous porous materials under study can be saturated by fluids with pre-set thermal conductivity, and a greater number of physical property values can be obtained experimentally (thermal conductivity and other properties, including, for instance, elastic wave velocities, electric conductivity, hydraulic and dielectric permeability, density, and volumetric thermal capacity) to be used for determination of unknown parameters, pore space characteristics and matrix thermal conductivity.

Thermal conductivity of mixtures may be determined (either by measurement or calculation) and is known for each mixture. Thermal conductivity of such mixtures may have different values, each of which may be pre-selected so as to meet certain requirements in conformity with thermal conductivity, porosity and pore space parameters of heterogeneous porous materials under study. In addition, the requirement that thermal conductivity of such mixtures remains within a certain range of values can be met, and such a range can be pre-selected depending on thermal conductivity, porosity and pore space characteristics of the heterogeneous porous materials under study. The use of mixtures of two or more fluids with different thermal conductivity values, including pre-set values adds to the number of saturating substances and eliminates the requirement for porosity of a porous material sample to be a known value. Instead, it could be one of the values subject to determination along with pore space characteristics and thermal conductivity of the matrix.

A sample of a porous material is alternately saturated by at least two saturating fluids with different known thermal conductivities, at least one of the saturating fluids is a mixture of at least two fluids with different known thermal conductivities. Each time after the sample is saturated, thermal conductivity of the saturated sample of the porous material is measured, and pore space characteristics and thermal conductivity of a matrix of the porous material sample are determined taking into account results of thermal conductivity measurements. The pore space characteristics comprise porosity and pore space geometry. In another embodiment of the disclosure, porosity of porous material samples may be preliminary determined.

Thermal conductivity of the fluid mixture can be preliminary determined by known thermal conductivity values of each fluid in the mixture and their volume or mass proportion in the mixture. According another embodiment of the disclosure thermal conductivity of the fluid mixture can be determined by measuring thermal conductivity of the fluid mixture after the fluids have been mixed.

In accordance with another embodiment of the invention the thermal conductivity value of the fluid mixture or a range thereof is preliminary known.

Oil and water can be used as the saturating fluids.

A gas with a known thermal conductivity (for instance, air) may be used as at least one fluid. When using at least two fluid mixtures containing gas with known thermal conductivity, different thermal conductivities of the fluid mixtures are provided by using the same gas with different humidity.

In one embodiment of the disclosure, the appropriate thermal conductivity values of fluids are preliminary determined, as well as a number of mixtures to be prepared and thermal conductivity values of the mixtures to be prepared.

According another embodiment of the disclosure after each saturation of the sample of the porous material at least one additional physical property of the sample is determined, and the results of determination of such additional physical property are used in combination with the results of determination of thermal conductivity of the sample to determine the pore space characteristics and thermal conductivity of the porous sample matrix.

The additionally determined physical property of the sample is at least one property selected from the following group: elastic wave velocity, electric conductivity, permeability, density, and volumetric thermal capacity.

The thermal conductivity of the saturated sample can be determined by method of optical scanning.

BRIEF DESCRIPTION OF DRAWINGS

The invention is illustrated with the drawings wherein.

DETAILED DESCRIPTION

Figure 1:
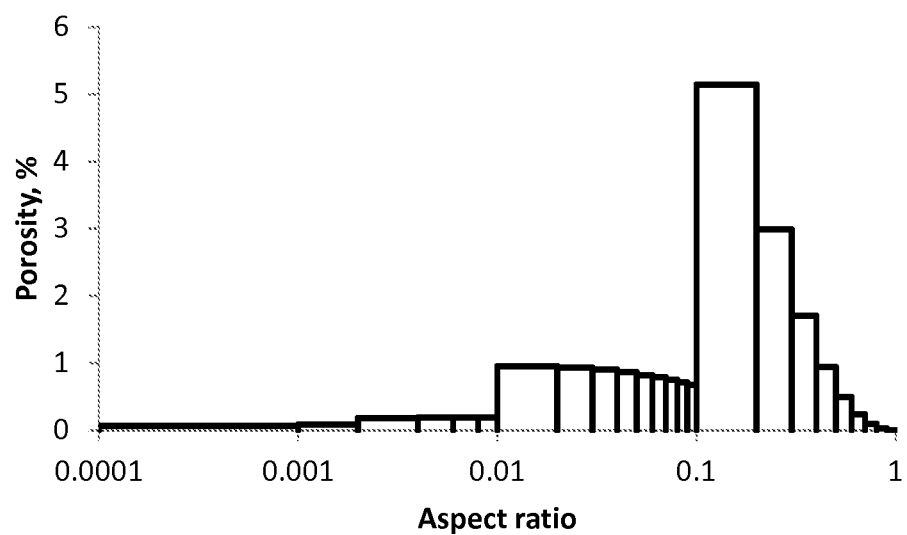
FIG. 1 shows a distribution of voids by aspect ratios built on the basis of beta-parameters ($\alpha=3.0$, $\beta=1.1$) determined in the case when sample porosity value was unknown and had to be determined along with the beta distribution parameters and matrix thermal conductivity.
Figure 2:
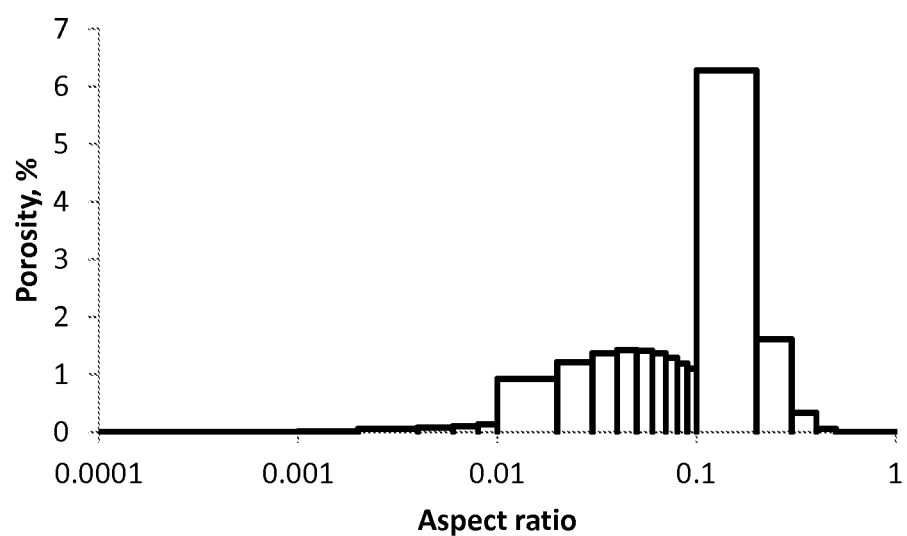
FIG. 2 shows a distribution of voids by aspect ratios built on the basis of beta-parameters ($\alpha=7.1$, $\beta=1.8$) determined in the case when sample porosity value was preliminary known.

A sample of a porous material is alternately saturated by one or several saturating fluids with known thermal conductivity, and thermal conductivity of the saturated porous sample is measured. Then, the sample is additionally saturated by at least one mixture of two or more fluids with different known thermal conductivities. Each time after the sample is saturated its thermal conductivity is measured. The measured thermal conductivity values of the sample saturated by one or several mixtures of two or more fluids are used to determine characteristics of a pore space and thermal conductivity of a porous sample matrix. The pore space characteristics comprise porosity and geometric parameters of the porous space (for instance, aspect ratio of void-simulating ellipsoids, parameters of pore and crack aspect ratio distribution function or of any other values characterizing the shape of pores and cracks by volume, orientation or size).

The porosity, pore space geometric parameters, and matrix thermal conductivity are determined for the sample in such a way as to keep a difference between thermal conductivity values experimentally obtained each time after sample saturation and its theoretical values below or equal to a given value. Theoretical values of thermal conductivity of the porous material sample in dependence of porosity, geometric parameters of the pore space and thermal conductivity of the matrix are determined by known formula linking the value of thermal conductivity of a porous sample to the values of porosity, geometric parameters of the pore space and thermal conductivity of the matrix. For instance, formulas known from the effective-medium theory may be used for that purpose as shown below.

Let's assume that thermal conductivity measurements are taken in a certain direction defined by vector $n=(n_1, n_2, n_3)$ in the main coordinate system. The main coordinate system is determined by symmetry elements of a porous material sample with the effective tensor of thermal conductivity having a diagonal shape. Then, thermal conductivity value in that direction is determined by the following known formula:

$$\lambda^{*(n)} = \lambda^*_{ij} n_i n_j = \lambda^*_{11} n_1^2 + \lambda^*_{22} n_2^2 + \lambda^*_{33} n_3^2, \qquad (1)$$

where $\lambda^*$—an effective tensor of thermal conductivity in the main coordinate system linked to porosity $\phi$, pore space geometric parameters defined by tensor g, and the matrix thermal conductivity tensor $\lambda^M$ in the following way (Popov et al., Interrelations between Thermal Conductivity and Other Physical Properties of Rocks: Experimental Data. Pure Appl. Geophys., 160, 2003, pp. 1137-1161):

$$\lambda^* = [(1-\phi)\langle \lambda^M(r)[I-g^M(\lambda^M(r)-\lambda^c)]^{-1}\rangle + \phi \langle \lambda^F(r)[I-g^F(\lambda^F(r)-\lambda^c)]^{-1}\rangle] \times [(1-\phi)\langle [I-g^M(\lambda^M(r)-\lambda^c)]^{-1}\rangle + \phi \langle [I-g^F(\lambda^F(r)-\lambda^c)]^{-1}\rangle]^{-1} \qquad (2)$$

Angular brackets in formula (2) indicate volumetric averaging, which in the case of a statistically homogeneous medium may be replaced by statistical ensemble averaging; $\lambda^F(r)$—fluid thermal conductivity tensor in point r of a porous/cracky material sample; I—identity matrix. Tensor g components take the form:

$$g_{kl} = -\frac{1}{4\pi} \int n_{kl} \Lambda^{-1} d\Omega, \quad (3)$$

where $n_{kl} \equiv n_k n_l,$ $n_1 = \frac{1}{a_1} \sin\theta\cos\varphi,$ $n_2 = \frac{1}{a_2} \sin\theta\sin\varphi,$ $n_3 = \frac{1}{a_3} \cos\theta,$ $d\Omega \equiv \sin\theta d\theta d\varphi,$ and $\alpha_i$—semi-axes of ellipsoids simulating mineral grains (Index M), pores and cracks (Index F); $\Lambda \equiv Xf_jn_in_j$, $\theta$ and $\varphi$—polar and azimuth angle in the spherical coordinate system; $\lambda^c$—thermal conductivity tensor of a reference body. The choice of a reference body results in different formula of the effective-medium theory methods, including that of self-consistency assuming $\lambda^c = \lambda^*$ (Popov et al. Interrelations between Thermal Conductivity and Other Physical Properties of Rocks: Experimental Data. Pure Appl. Geophys., 160, 2003, pp. 1137-1161), the Hashin-Strikman method (Bayuk I., Gay J., Hooper J., and Chesnokov E. Upper and Lower Stiffness Bounds for Porous Anisotropic Rocks, Geophysics Journal International, 175, 2008, pp. 1309-1320) in which property values of the reference body are assumed equal to those of a mineral or fluid, depending on the rock inner composition. The choice of a reference body in the form of $\lambda^c = (1-f)\lambda^M + f\lambda^F$, where f is a certain constant value facilitates determination of a degree of pore space connectivity (Bayuk I. and Chesnokov E. Identification of the Fluid Type in a Reservoir Rock, Journal of the Solid Earth, 35, Nr. 11, 1999, pp. 917-923).

Porous sample porosity, the geometric parameters of the pore space and thermal conductivity of the matrix may be determined from the measured thermal conductivity values of the fluid-saturated porous sample, for instance, by minimizing a function characterizing the difference between theoretical and experimentally obtained thermal conductivity values for the porous sample by measurements taken each time after its saturation. Such a function could be, for instance, a sum of squares or a sum of absolute values of the numbers representing the difference between theoretical and experimentally obtained thermal conductivity values, the summing up of which is based on the number of thermal conductivity measurements taken for the saturated porous material sample. Another example of a solution procedure for porous sample porosity, pore space geometry and matrix thermal conductivity is to accumulate all the values of porosity, geometric parameters of pore space, and matrix thermal conductivity for which the difference between theoretical and experimental thermal conductivity values obtained for the porous sample by measurements taken each time after its saturation does not exceed a certain pre-assigned value, and make subsequent calculations to determine statistical characteristics of the accumulated values of porosity, pore space geometric parameters, and thermal conductivity of the pore sample matrix.

In one of embodiments, thermal conductivity of a mixture of two or more fluids is determined from known thermal conductivity of each of the two or more fluids and their volumetric or mass ratios in the mixture. Thermal conductivity of a mixture of N fluids may be determined by the so-called theoretical model for the average, which takes the form (U.S. Pat. No. 5,159,569. Formation Evaluation from Thermal Properties. H. Xu and R. Desbrandes, 1992):

$$\lambda_{cMecu} = \sum_{i=1}^{i=N} S_{\text{флюида} i} \cdot \lambda_{\text{флюида} i},$$

where $\lambda_{cmecu}$—thermal conductivity of the mixture of N fluids, N—the number of fluids in the mixture, $S_{\text{флюида} i}$—a relative volumetric content of an i-th fluid in the mixture, $\lambda_{\text{флюида} i}$—a thermal conductivity of the i-th fluid.

In order to simplify preparation of mixtures of two or more fluids with a certain pre-assigned thermal conductivity value, mixtures of at least two fluids are prepared, and then, after preparation of each such mixture, its thermal conductivity is determined by experiment. Thermal conductivity of the prepared mixture can be determined by any conventional method for measuring fluid thermal conductivity, for instance, using the DTC-25 Thermal Conductivity Analyzer manufactured by Intertech Corporation (US).

According another embodiment of the disclosure, for each of the mixtures of two or more fluids appropriate thermal conductivity values or a range thereof are additionally specified. The thermal conductivity values or a range thereof for each mixture are specified based on necessary difference between thermal conductivities of one or several saturating fluids and of various mixtures. The necessary difference between thermal conductivities of saturating fluids and their mixtures is selected in such a way as to ensure a stable solution to the problem of determination of porosity, pore space geometry, and matrix thermal conductivity based on thermal conductivity measurements of a fluid-saturated porous sample, and necessary accuracy of porosity, pore space geometry, and matrix thermal conductivity determination.

Gas or multiple gases can be used as at least one of the fluids in the mixture, and air may be used as the gas.

In the latter case, variations of thermal conductivity of the mixture of the fluids and the gas with known thermal conductivity and obtaining of necessary thermal conductivity of this mixture can be provided by changing humidity of the gas by additional saturation of the gas with one or several fluids.

In accordance with one embodiment of the disclosure, necessary thermal conductivity values of two or more initial fluids, a number of mixtures of the initial fluids to be prepared, and necessary thermal conductivity values of such mixtures of the initial fluids are preliminary determined, with due consideration of thermal conductivity of one or several saturating fluids and based on a stable solution of a reverse problem of characterizing pore space and matrix thermal conductivity of the porous material sample, and the accuracy of measurements of thermal conductivity of fluids, of fluid mixtures, and of the sample after its saturation. The necessary thermal conductivity values of two initial fluids, the number of the mixtures of the initial fluids and the necessary thermal conductivity values of the mixtures can be determined, for instance, by requiring that the following three conditions be met concurrently. The first condition is that thermal conductivity of the mixtures of selected fluids should differ by an amount exceeding the accuracy of thermal conductivity measurement in a method used to measure thermal conductivity of the mixture of two selected fluids. For example, when using a linear source method providing for a 10% error in measuring thermal conductivity of fluids, thermal conductivities of the mixtures of the selected fluids should differ by more than 10%. The second condition is that thermal conductivity values of the sample after its each saturation calculated by a theoretical method used to characterize pore space and matrix thermal conductivity of the porous material sample should differ by an amount exceeding the accuracy of thermal conductivity measurement in a method used to measure thermal conductivity of the saturated porous sample. For instance, theoretical thermal conductivity values calculated for a porous material sample saturated by various mixtures of two selected fluids should differ by more than 3% if thermal conductivity of the sample was measured by method of optical scanning (the method accuracy is 2-3%). The third condition is that two or more fluids should be selected so as their thermal conductivity values allow for the existence of at least one mixture of two or more fluids meeting the first and the second condition.

In another embodiment, porosity of the porous material sample is additionally determined. The porosity is determined before or after measuring thermal conductivity of the sample successively saturated by one or several fluids and by at least one selected fluid mixture with known thermal conductivity. The values of thermal conductivity of the porous sample measured each time after its saturation and the known porosity value of the sample are used to determine pore space geometric parameters and matrix thermal conductivity of the porous sample. For that purpose known formulas are used linking the measured thermal conductivity with the known porosity, thermal conductivity of fluids and one or more fluid mixtures, pore space target geometrical characteristics, and thermal conductivity of the porous sample matrix.

The method can additionally provide for measurements of one or more additional physical properties of the porous material sample each time after its saturation by a fluid or a fluid mixture with known thermal conductivity. Such physical properties may include, for instance, elastic wave velocities, electric conductivity, hydraulic and dielectric permeability, density, and volumetric thermal capacity. After that, the results of determination of one or several additional physical properties of the sample are used to characterize the pore space and the matrix thermal conductivity of the sample together with the results of thermal conductivity determination. For that purpose, in addition to formulas (1)-(3) linking the measured thermal conductivity to the pore space geometric parameters, porosity, and matric thermal conductivity, similar formulas are used from the effective-medium theory linking the measured physical properties to the pore space geometric parameters, porosity, and appropriate physical properties of the matrix. Formulas for any efficient transport properties (electric conductivity, dielectric and hydraulic permeability) take a form similar to formulas (1)-(3) of effective thermal conductivity with thermal conductivity tensor replaced by electric conductivity, dielectric or hydraulic permeability tensor.

If elastic wave velocities are measured, the formulas linking their measured values to the pore space characteristics and the matrix thermal conductivity take the following form. If elastic wave velocities are measured in a certain direction set in the main coordinate system by vector $n=(n_1, n_2, n_3)$, then, elastic wave velocity values in that direction are determined through density and effective elastic tensor using the known Green-Christoffel equation:

$$\det(\Gamma_{ik} - \varrho(v^{(n)})^2 \delta_{ik}) = 0, \quad \text{where} \tag{4}$$

$$\Gamma_{ik} = C^*_{ijkl} n_j n_l. \tag{5}$$

In formulas (4) and (5), $v^{(n)}$—a velocity of a longitudinal and shear wave in the direction n, $\rho$—density, $\delta_{ik}$—Kronecker Symbol, $C^*_{ijkl}$—components of an effective elastic tensor. The effective elastic tensor is determined by a formula similar to formula (2), with thermal conductivity tensors replaced by elastic tensors; second-rank identity, by fourth-rank identity tensor; the second-rank tensor g by the fourth-rank tensor g which takes the form $$g_{kmln} = \tilde{a}_{k)(l,n)(m}, \quad \tilde{a}_{k)(l,n)(m} \equiv \frac{1}{4}(a_{klnm} + a_{mlnk} + a_{knlm} + a_{mnlk}), \tag{6}$$

$$\tilde{a}_{kmln} = \frac{1}{4\pi}\int n_{mn}\Lambda_{kl}^{-1}\sin\theta d\theta d\varphi,$$

$$\Lambda_{kl} \equiv C^*_{kmln}n_{mn},$$

$$n_{mn} \equiv n_m n_n,$$

$$n_1 = \frac{1}{a_1}\sin\theta\cos\varphi,$$

$$n_2 = \frac{1}{a_2}\sin\theta\sin\varphi,$$

$$n_3 = \frac{1}{a_3}\cos\theta.$$

If volumetric thermal capacity or porosity is measured along the porous/cracky material sample, e ratios of their measured values to appropriate values of the matrix, saturated fluid, and porosity take the form $$(c\rho)^{(n)} = (c\rho)^* \tag{7}$$
$$= (1-\phi)(c\rho)^M + \phi(c\rho)^F,$$

$$\rho^{(n)} = \rho^* \tag{8}$$
$$= (1-\phi)\rho^M + \phi\rho^F.$$

The volumetric capacity and porosity does not depend on the pore space geometric parameters.

Porous sample porosity, pore space geometric parameters and matrix thermal conductivity may be determined from the measured thermal conductivity values of the fluid-saturated porous sample, for instance, by minimizing the function characterizing a difference between theoretical and experimentally obtained values of thermal conductivity and other physical properties measured for the porous sample each time after its saturation. Such a function could be, for instance, a sum of squares or a sum of absolute values of the numbers representing relative differences between theoretical and experimentally obtained thermal conductivity and other physical property values, the summing up of which is based on the number of physical property measurements taken. Another example of a solution procedure for porous sample porosity, geometric parameters of pore space, and matrix thermal conductivity is accumulation of all the values of porosity, pore space geometry and matrix thermal conductivity for which the difference between theoretical and experimental thermal conductivity and other physical property values obtained for the sample by measurements taken each time after its saturation does not exceed a certain specified value, and make subsequent calculations to determine statistical characteristics of the accumulated values of porosity, pore space geometry, and thermal conductivity of a pore sample matrix.

A following example demonstrates one of the embodiments of the disclosure. Pore space characteristics and a matrix thermal conductivity should be determined for a carbonate reservoir rock sample having 5 cm in length and 5 cm in width. Water and oil with thermal conductivities of 0.6 and 0.12 W/(mK) are chosen as saturating fluids. A total of five mixtures were prepared of those fluids with water/oil ratios of 0.9/0.1 (Mixture 1), 0.6/0.4 (Mixture 2), 0.4/0.6 (Mixture 3), 0.2/0.8 (Mixture 4) and 0.0/1.0 (Mixture 5). Thermal conductivity of a two-fluid mixture is determined by method of a linear source, and its measured values are 0.50, 0.30, 0.22, 0.15 and 0.12 W/(mK) for Mixtures 1 to 5, respectively. The difference between thermal conductivity values of the mixtures is over 15%, which exceeds the accuracy of the linear source method (10%). The sample is successively saturated under vacuum pressure by each mixture. A vacuum pressure facility is used to ensure full water saturation of connected pores and cracks. Thermal conductivity of the fluid-saturated sample is measured by method of optical scanning each time after its saturation. After each thermal conductivity measurement the sample is extracted (for oil removal) and dried to 105° C., following which it is saturated with the next mixture. Measured thermal conductivity values of the sample saturated by Mixtures 1 to 5 equal 2.19, 2.04, 1.93, 1.83 and 1.77 W/(mK), respectively. The difference between thermal conductivity values of the sample saturated by different mixtures exceeds the accuracy of the linear source method (2-3%). The resulting thermal conductivity values are used to determine pore space geometric parameters, porosity, and matrix thermal conductivity. The shape of cracks and pores governing the value of g in equation (3) are simulated by spheroids characterized by an aspect ratio. In that case, it would be convenient to use depolarization factor D linked to aspect ratio by the following formula:

$$D = \frac{1 - D_3}{2}.$$

In the case of oblong spheroids with aspect ratio κ exceeding 1, the following formula $$D_3 = (1 - e^2)\frac{Arth(e) - e}{e^3}, e = \sqrt{\frac{\kappa^2 - 1}{\kappa^2}}$$

will apply, and in the case of oblong spheroids with aspect ratio κ below or equal 1, $$D_3 = (1 + e^2)\frac{e - arctg(e)}{e^3}, e = \left[\frac{1 - \kappa^2}{\kappa^2}\right]^{1/2}$$

will apply. Crack/pore volume distribution over depolarization factor is described by the two-parametric Beta-distribution function $$P(F) = \frac{\Gamma(\alpha + \beta)}{\Gamma(\alpha)\Gamma(\beta)} F^{\alpha - 1}(1 - F)^{\beta - 1},$$

where Γ is the gamma-function. The Beta-distribution parameters α and Γ are non-negative and are assumed as unknown. Provided that the rock is isotropic, its pore/crack orientation is assumed as chaotic.

The unknown values in formula (2) are two Beta-distribution parameters, matrix thermal conductivity and effective porosity. In order to find a solution, a potential variation range is pre-assigned to each unknown value. Such a variation range for each of the Beta-distribution parameters is the interval [0.0001; 100]. For this sample, the 15-25% porosity value range is selected based on log data on porosity in the depth interval of the sample origin. Matrix thermal conductivity differs from thermal conductivity determined on the basis of mineral composition because a carbonate reservoir may contain isolated pores, organic debris, and capillary water. The range of matrix thermal conductivity is assigned within the range of its potential values, 2.5-3.5 W/(mK). The unknown Beta-distribution parameters, matrix thermal conductivity and effective porosity are determined by minimizing the sum of relative differences between theoretical and experimentally obtained values of thermal conductivity for each saturating fluid. For the purpose of minimization, a version of the deformed polyhedron method is used covering the potential variation range of the target parameters. FIG. 1 shows void distribution by aspect ratios based on the determined values of the Beta-distribution parameters. The matrix thermal conductivity value as determined equals 2.96 W/(mK); effective porosity, 20%. The determined effective porosity value proves identical to the porosity value subsequently measured in that sample by the Archimedean method in order to verify the proposed technique.

Thermal conductivity of a fluid mixture (for instance, oil/water) may be determined by the known Lichtenecker method (Lichtenecker, K. and K. Rother, "Die Herleitung des Logarithmischen Mischungsgesetzes aus Allgemeinen Prinzipien des Stationären Strömung", Phys. Zeit, 1931, 32, 255-260).

Fluid mixtures can be prepared in such a way that their thermal conductivity values do not exceed a halved thermal conductivity value calculated on the basis of known thermal conductivity and volumetric concentration values of matrix components. That thermal conductivity value is determined by the Lichtenecker method.

When using air as one of the initial fluids, several mixtures can be prepared by changing air humidity so as to have at least 10% difference between thermal conductivity values of such mixtures.

Matrix thermal conductivity may be initially determined on the basis of known thermal conductivity values and volumetric concentration of matrix components. For that purpose, the known Lichtenecker method is used. Then, initial saturating fluids are selected so that thermal conductivity of one of the fluids differs from the estimated matrix thermal conductivity not less than by an order of magnitude and thermal conductivity of the second fluid—not less than five times. Sample porosity is at least 10%. At that, thermal conductivity values of fluids differ more than twice. One or more mixtures of two such fluids is prepared in such a way that thermal conductivity of each mixture differ by at least 15% from thermal conductivity of any other mixture and of pure fluids. That value exceeds the accuracy of thermal conductivity measurement of fluids by the linear source method (10%). Thermal conductivity of each mixture differs from estimated matrix thermal conductivity not less than twice. Such contrasts in properties of saturating fluids and mixtures thereof guarantee that the difference in thermal conductivity values of the porous sample saturated by each fluid and mixture or mixtures thereof will exceed the accuracy of thermal conductivity measurements by method of optical scanning (2-3%) used to measure thermal conductivity of saturated porous samples. Significant difference in thermal conductivity values of the porous sample saturated by each fluid and mixture or mixtures thereof facilitates a stable solution of a reverse problem of characterizing pore space and matrix thermal conductivity of a porous material sample.

Another embodiment is illustrated by the following example of known porosity of carbonate reservoir rock sample. Thermal conductivity measurements are taken for the same sample and using same saturating mixtures of two fluids (water/oil) as those in the previous example. Thermal conductivity of fluid mixtures, like in the previous case, is measured by method of linear source. Porosity measured by the Archimedean method is 20%. The unknown values in formula (2) are two Beta-distribution parameters and matrix thermal conductivity which are determined by minimizing the sum of relative differences between theoretical and experimentally obtained values of thermal conductivity for each saturating fluid. The matrix thermal conductivity value as determined equals 2.98 W/(mK). Void distribution by aspect ratios is determined by Beta-distribution parameters as shown in FIG. 1b.

In addition to thermal conductivity, other properties can be measured as well, for instance, velocities of longitudinal and shear elastic waves and electric conductivity of the sample. The measured values are used for determination of the pore space and matrix thermal conductivity.

The invention claimed is:

1. A method for determining pore space parameters and a thermal conductivity of a matrix of a porous material sample, the method comprising:
   alternately saturating the sample of the porous material by at least two saturating fluids with different known thermal conductivities, at least one of the saturating fluids being a mixture of at least two fluids with different known thermal conductivities,
   measuring a thermal conductivity of the saturated sample of the porous material after each saturation; and
   determining the pore space parameters and the thermal conductivity of the matrix of the sample of the porous material using the measured thermal conductivities of the saturated sample of the porous material.

2. The method of claim 1, wherein the pore space parameters comprise a porosity and pore space geometric parameters.

3. The method of claim 1, wherein a porosity of the sample of the porous material is preliminary determined.

4. The method of claim 1, wherein a thermal conductivity of the mixture of the at least two fluids is preliminary determined from the known thermal conductivity values of each fluid of the mixture and a volumetric or a mass ratio of the fluids in the mixture.

5. The method of claim 1, wherein a thermal conductivity of the mixture of the at least two fluids is preliminary determined by measuring the thermal conductivity of the mixture after mixing the at least two fluids.

6. The method of claim 1, wherein a thermal conductivity of the mixture of the fluids or a range of thermal conductivities of the mixture of the fluids is preliminary specified.

7. The method of claim 1, wherein oil and water are used as the saturating fluids.

8. The method of claim 1, wherein the thermal conductivities of the saturating fluids and a number of the mixtures of the fluids are preliminary determined.

9. The method of claim 1, wherein the thermal conductivity of the saturated sample is determined using optical scanning.

10. The method of claim 1, wherein a gas is used as at least one fluid in the mixture of the at least two fluids with the different known thermal conductivities.

11. The method of claim 10, wherein air is used as the gas.

12. The method of claim 1, wherein at least two mixtures of the at least two fluids with the different known thermal conductivities are used, each mixture comprising a gas, and the different thermal conductivity values of the mixtures are provided by using the same gas with different humidity.

13. The method of claim 12 wherein air is used as the gas.

14. The method of claim 1, wherein at least one additional physical property of the sample of the porous material is measured after each saturation of the sample, and the results of the measurements are used to determine the pore space parameters and the thermal conductivity of the matrix of the sample of the porous material.

15. The method of claim 14, wherein the at least one additional physical property is selected from the group consisting of: elastic wave velocities, electric conductivity, permeability, density, and volumetric thermal capacity.

* * * * *